(12) United States Patent
Perez

(10) Patent No.: US 9,283,329 B2
(45) Date of Patent: Mar. 15, 2016

(54) HYPODERMIC SYRINGE GUIDE

(76) Inventor: James Gerard Perez, Bonita, CA (US)

( * ) Notice: Subject to any disclaimer, the term of this patent is extended or adjusted under 35 U.S.C. 154(b) by 2072 days.

(21) Appl. No.: 11/557,494

(22) Filed: Nov. 8, 2006

(65) Prior Publication Data

US 2007/0233010 A1 Oct. 4, 2007

Related U.S. Application Data

(60) Provisional application No. 60/788,747, filed on Mar. 30, 2006.

(51) Int. Cl.
*A61M 5/00* (2006.01)
*A61M 5/32* (2006.01)
*A61M 5/42* (2006.01)

(52) U.S. Cl.
CPC ........... *A61M 5/3287* (2013.01); *A61M 5/3243* (2013.01); *A61M 5/425* (2013.01); *A61M 2005/3252* (2013.01)

(58) Field of Classification Search
CPC ..... A61M 5/425; A61M 5/427; A61M 5/345; A61M 5/3293; A61M 5/3243; A61M 5/346; A61M 5/3271; A61M 2005/3252; A61M 2005/323; A61M 2005/3228

USPC .......... 604/110, 115–117, 187, 192, 197, 198
See application file for complete search history.

(56) References Cited

U.S. PATENT DOCUMENTS

| | | | | |
|---|---|---|---|---|
| 2,047,010 | A | * | 7/1936 | Dickinson ..................... 604/157 |
| 4,403,987 | A | * | 9/1983 | Gottinger ...................... 604/115 |
| 5,279,581 | A | * | 1/1994 | Firth et al. .................... 604/198 |
| 5,911,707 | A | * | 6/1999 | Wolvek et al. ................ 604/116 |
| 5,951,523 | A | * | 9/1999 | Osterlind et al. ............. 604/192 |
| 8,758,300 | B2 | * | 6/2014 | Bakhtyari-Nejad-Esfahani 604/117 |
| 2001/0044606 | A1 | * | 11/2001 | Inkpen et al. ................. 604/181 |
| 2006/0211987 | A1 | * | 9/2006 | Williams ....................... 604/116 |
| 2008/0269677 | A1 | * | 10/2008 | Cull ............................... 604/116 |

* cited by examiner

*Primary Examiner* — Nathan R Price
*Assistant Examiner* — Justin L Zamory

(57) ABSTRACT

An arterial syringe guide adapted for use with a common arterial syringe is provided for improving the safety of the arterial sampling procedure, for providing easy access to a syringe blood receptacle, and for facilitating the insertion of the needle of a syringe into a targeted artery. An integrated artery stabilizer holds the artery in place during use. A syringe holder retains the needle hub of a hypodermic needle. The blood receptacle component of the employed syringe may be separated from the device, leaving the needle component of the syringe locked on the device for safety.

8 Claims, 15 Drawing Sheets

HYPODERMIC SYRINGE GUIDE

This application claims the benefit of U.S. Provisional Application No. 60/788,747 filed on Mar. 30, 2006.

BACKGROUND OF THE INVENTION

1. Field of Invention

This invention relates generally to syringe guide devices, specifically to a device with a needle-shielding syringe guide that can be adapted for use with one of a variety of common arterial syringes and that allows quick release of a syringe blood receptacle.

2. History of Technology

In order to insert the needle of a syringe into a targeted artery, a medical technician will often struggle with instability of the artery during the procedure; the artery may tend to move away from an incoming needle. A second problem is that the artery may be hard to locate. A third common problem is that safety is jeopardized by an over-exposed needle. A fourth problem is that it is difficult to maintain a straight path of insertion. A fifth problem is that it is impossible to keep exposed fingers away from the puncture site. The present invention solves these problems.

The withdrawal of arterial blood from a patient is a common procedure in today's health care settings. Arterial blood gas, or "ABG" analysis serves to provide vital information concerning the respiratory status of the patient. Blood is drawn anaerobically from an artery such as the radial, brachial, femoral, or dorsalis pedis artery, via a percutaneous needle puncture. The preferred site is the radial artery. A blood specimen is collected for direct measurement of the partial pressures of carbon dioxide (PaCO2) and oxygen (PaO2), hydrogen ion activity (pH), total hemoglobin (Hbtotal), oxyhemoglobin saturation (HbO2), and the dyshemoglobins carboxyhemoglobin (COHb) and methemoglobin (MetHb). Sampling typically may only be performed by trained and certified health care personnel.

A modified Allen Test (collateral circulation test) should always be performed by a technician before the technician inserts a needle into a patient's radial artery. The Allen Test determines if blood is capable of flowing through the ulnar artery. The ulnar artery is the only other source of blood to the hand aside from the radial artery. A negative test result is indicative of inadequate collateral blood supply to the hand and requires the selection of another location as the site for arterial access.

To obtain an arterial blood sample, the technician will first determine the precise location in which to insert the needle of a syringe into the artery of the patient. Once an appropriate site is located, the needle is inserted by the technician into the selected artery until the artery is penetrated and the syringe's blood receptacle fills with sufficient blood. Then, the needle is removed from within the artery, the wound is dressed, and the needle is capped to prevent needle injuries. The arterial blood draw process is difficult and prone to errors, even when the technician has ample experience. Because of the traumatic nature of the procedure, and the large number of complications that may arise, it is important for the technician to try to obtain the arterial blood properly and effectively on the first attempt. Prior art has seriously failed to provide technicians with adequate means to obtain a successful arterial blood sample regularly on the first attempt.

An unrestrained artery may tend to move away from an incoming needle, particularly in older patients whose skin has lost elasticity. A loss of elasticity in the skin creates a loss of stability around the artery, which allows the artery to roll around under the surface of the skin. It is possible for a needle tip to push the artery away from its path, causing the technician to miss the targeted artery completely. The present invention solves this problem by providing an artery stabilizer to hold the artery in place.

Currently, the technician will press her or his finger over the anticipated arterial puncture site and then estimate where the artery lies under that finger; it is a rough estimate and the technician often miscalculates. Alternatively, the technician may place two fingers over the artery and attempt to hold the artery between the fingertips, inserting the needle between the two fingertips to penetrate the artery. This method has its limitations; the technician should have a tight pair of gloves, cannot have long finger nails, and will rely on bulky fingertips to pinpoint a relatively thin artery between them, and this technique is impossible to use on infants and small children. The present invention uses an artery stabilizer to hold the artery within two integrated stabilizer fingers at the base of the device, and it partially occludes the artery during use; this creates an augmented pulse at the site where the needle will enter the artery, simplifying palpation of the artery and vastly diminishing the labor involved in identifying where to insert the needle. The artery stabilizer further allows the technician to keep any of the technician's exposed extremities substantially away from the puncture site while inserting the needle into the targeted artery, thus improving safety.

Because of low blood pressure, a patient's pulse may be weak and hard to locate. It is sometimes necessary for the technician to perform an arterial puncture "blindly," merely stabbing the site where the technician considers the best option for obtaining arterial access. The present invention helps to create an augmented pulse that is palpable even in cases of low blood pressure.

Most ABG protocols allow a technician to try three consecutive needle insertions without removing the needle tip beyond the subcutaneous tissue. As the angle of insertion changes within the dermis, the needle slices through the tissue in its path, and may even lacerate the artery. Any change in the angle of needle insertion can inflict severe pain onto a conscious patient. Because of the structural design of the present invention, a straight, unswerving path of needle insertion into the artery is achieved. Currently, the often unsteady hand of the technician is used to guide the syringe needle down into the artery. A nervous hand can become quite jittery, and even a calm hand does not guarantee a straight path of insertion into and out of the vessel. The present invention provides a considerable improvement in this regard; pressing the artery stabilizer, at the base of the invention, down near the puncture site provides stability to the hand of the technician. The straight slot within the housing, which supports the syringe, vastly improves the likelihood of a direct and controlled line of insertion and extraction of the needle during a blood draw procedure, minimizing pain and trauma within the patient's dermal tissues and artery.

Often, the unrestrained nature of the current methods for inserting a needle into an artery causes the needle to become accidentally extracted from within the artery during a blood draw attempt, causing a cessation of blood flow. The present invention prevents this common mishap, by providing a solid, steady housing within which the syringe is securely held in place during the procedure.

According to standard ABG protocols, a needle should enter an artery at a steady angle of approximately 45 degrees in relation to the artery distal the heart near the insertion site; prior art relies on the technician to maintain that angle without any support. A proper angle of needle insertion is assured using the present invention, as a result of the base of the stabilizer fingers being properly angled in relation to the housing slot within which the syringe is maneuvered.

PRIOR ART

Generally, prior art may include devices which guide a syringe into and out of a blood vessel, and also any device which is designed to stabilize a blood vessel during a needle puncture of that vessel. Most precisely, prior art includes any device that stabilizes an artery during the insertion of a needle into the artery. It is important to note that an artery is not a vein; devices used for venous access are typically used for injections while arterial access is typically sought for arterial blood collection. Arteries have a pulse while veins do not. Arteries carry blood from the heart while veins carry blood back to the heart. Arteries are deep within the body while veins used for venous access are shallower. For arterial blood collection it is important to be able to detach the syringe barrel from the syringe needle in order to analyze the blood collected in the barrel. Furthermore, where a free-handed approach is acceptable with venous access, since veins are closer to the surface of the skin, the deeper location of an artery makes a free-handed needle insertion difficult; stabilizing the syringe and the targeted artery are crucial steps in preventing undue damage to the patient's tissues. An artery stabilizer and means to press the device down firmly at the targeted arterial access site are helpful components included in the present invention.

The number of devices within the realm of prior art related specifically to artery stabilizer devices is currently very limited; a vast majority of devices are directed at venous access. One device, described by Ayer, is an invention that presses two protrusions down on each side of a targeted portion of a radial artery in order to hold the artery in place and prevent the artery from moving away from an incoming needle. The Ayer device requires a band to be strapped around the wrist of the patient. This band may tend to occlude the ulnar artery and thus restrict vital collateral blood flow through the ulnar artery to the hand. If the radial artery becomes occluded during the blood draw procedure, complete absence of blood flow to the hand can result, causing tissue trauma or death within that extremity. The current invention does not require a band to be secured around the wrist; more advantageously, the invention is held in place by the technician, thereby eliminating the risk of impeding the collateral blood flow through the ulnar artery when the radial artery is targeted. Another benefit over the Ayer device is that the present invention may be used on any artery, not just the radial artery. Unlike the Ayer device, the present invention includes a syringe guide to help guide the needle of the syringe steadily into and out of the artery. Another limitation of the Ayer device is that it maintains a constant pressure over the targeted artery. As a result, it is not possible to reduce that pressure when it is time to withdraw the needle from the puncture site; the augmented pulse pressure can cause increased blood spillage out of the wound when the needle is removed. The present invention allows the technician to release the pressure over the artery before removing the needle from the puncture site.

Most of the devices within the realm of prior art do not address the issue of safety adequately. Most syringes require the integrated needle to be exposed during much of the procedure; this can be hazardous to technicians and patients if the syringes are handled improperly or unsteadily, as may commonly occur in emergency situations. Needle sticks are the most frequent source of transmission of blood borne disease in healthcare workers. In most of the devices of prior art, the needle is exposed before and after the insertion procedure and there are no means provided to protect personnel from contacting the needle during the procedure. Some devices allow needle retraction into a protective enclosure after a successful venous access, but these devices don't go far enough to prevent injuries, nor do they provide an artery stabilizer for stability and ease of use, and they are typically complex and expensive to manufacture. Most venous safety devices have self-retracting needles. The present invention uses a common syringe and accomplishes safety without the need for a self-retracting needle. With the present invention, the needle is exposed for only a brief instant during a blood draw procedure; the needle is lowered and exposed only after the device has been set over the targeted insertion site. Immediately after sufficient blood is obtained, the needle is safely withdrawn out of the artery and back into the protective walls of the housing.

Several devices have been proposed for stabilizing a vein for venipuncture, but none of the devices provide proper support for arterial puncture. For arterial puncture, the blood vessel stabilizer portion of the device should be relatively small to accommodate the limited space over the radial artery near the hand, it should be shaped to facilitate palpation of the targeted puncture site by the technician, and it should be shaped to allow the insertion of a needle proximal the patient's heart in relation to the stabilizer. The device should be designed to allow a proper angle of needle passage into the artery, and it should be easily removed from the puncture site; it cannot be bound or taped down during use. These features are all present in the current invention.

Unlike many of the devices of prior art, the present invention allows the use of any one of a large number of available syringes. The blood receptacle portion of the employed syringe may be detached from the needle and then capped with a syringe plug for transport. The current invention, with the needle safely held within its protective walls, can be discarded in a proper disposal container. The present invention may also implement an adjustable artery stabilizer to accommodate arteries of various sizes.

One possible embodiment of the current invention has a blood receptacle that is not required to be detached from the needle; following a blood draw, the needle is locked safely within the housing and the entire device is then transported for blood analysis. The technician removes a plug which caps the blood receptacle, to access the blood for analysis.

Objects and Advantages

Accordingly, several objects and advantages of the present invention include providing an artery stabilizing syringe guide that:

(a) holds a targeted artery in place for the insertion of a needle into the artery.

(b) isolates the artery and creates an augmented pulse for easy identification of its location.

(c) can be used with a large variety of common arterial syringes.

(d) supports a syringe and renders a straight path of needle penetration into and withdrawal from an artery.

(e) allows the needle of the syringe to be immobilized safely within the protective walls of the integrated housing or shield.

(f) is held in place by the technician and maneuverable using only one hand.

(g) assures a proper angle of needle insertion into the artery.

(h) allows unrestricted blood flow through the ulnar artery.

(i) helps the technician to keep the tip of the needle steadily within the artery.

(j) shields the technician's fingers from the sharp needle tip during use, to prevent injury.

(k) is inexpensive to manufacture, simple and intuitive to use, disposable, light-weight, and reusable if cleaned and disinfected properly.

(l) can be used on any individual of any age and size, and on any suitable artery.

(m) minimizes the need for multiple needle insertion attempts to penetrate the artery.

(n) allows the technician to regulate the pressure of the device over the artery, and to release the pressure before removing the needle from that artery.

(o) allows the technician to alter the width between each stabilizer finger.

DETAILED DESCRIPTION OF THE INVENTION

Figure 1A:
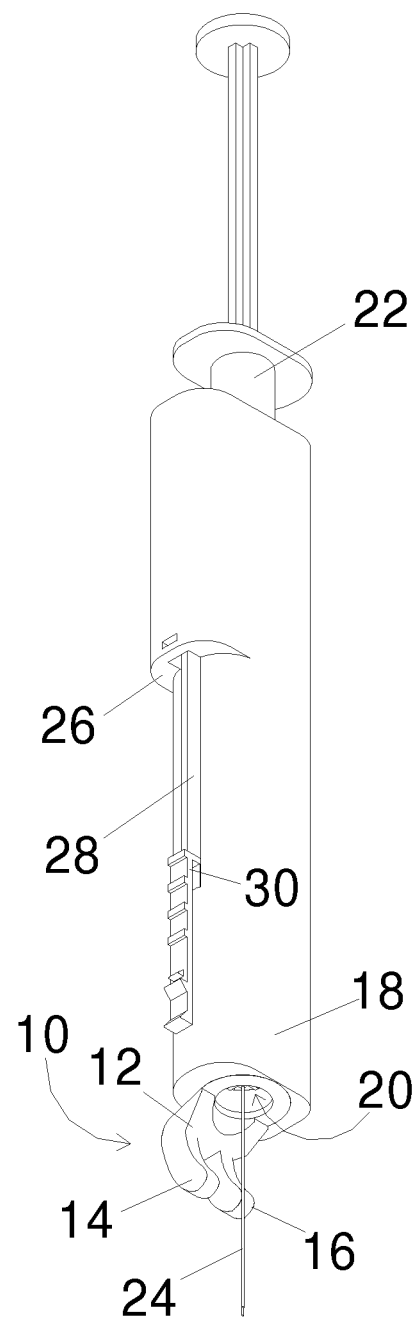
FIG. 1A is a perspective view of the invention, with a syringe attached to the syringe holder and lowered within the housing so that the needle of the syringe is exposed past the artery stabilizer.

Referring now to the drawings, FIGS. 1A-10 represent various embodiments and designs of the present invention. Each embodiment utilizes the novel feature of combining an artery stabilizer with a needle shielding syringe conveyor. Turning first to FIG. 1A, artery stabilizer 10 includes base 12 and stabilizer fingers 14 and 16; stabilizer fingers 14 and 16 emanate from base 12. A targeted artery is positioned by the technician between stabilizer fingers 14 and 16. Alternatively, only one stabilizer finger protrudes from base 12; the single finger would hold only one side rather than both sides of a targeted artery. For example, a single stabilizer finger would be pressed against one side of a radial artery while the patient's tendons would press up against the opposite side of the artery to hold the artery in place. Housing 18 is attached to base 12. Stabilizer fingers 14 and 16 serve to stabilize both a targeted artery and housing 18 during use. Slot 20 runs through housing 18. Syringe 22 is situated within slot 20 and lowered within slot 20 by the technician to guide needle 24 down into the targeted artery; needle 24 passes beyond and between the tips of stabilizer fingers 14 and 16 as shown. If one stabilizer finger is longer than the other, the needle would pass beyond the shorter of the stabilizer fingers where an augmented pulse is created by the stabilizer fingers over the artery. The bottom surface of each stabilizer finger (the part that contacts the patient) is angled relative to slot 20. The angle may be 45 degrees or any other angle suitable for the procedure. Housing bridge 26 connects each side of housing slit 28. Syringe holder arm 30 emanates through housing slit 28 from inside of slot 20 for access by the technician. A syringe may be supplied with the device, or alternatively, the device can be manufactured and distributed without a syringe; the device is capable of utilizing any of a large number of existing syringes, as will be made evident in the following discussion. Each embodiment of this invention is capable of being reused if it is cleaned and disinfected properly by qualified personnel. The device can be made of any transparent or semi-transparent solid material, like plastic.

Figure 1B:
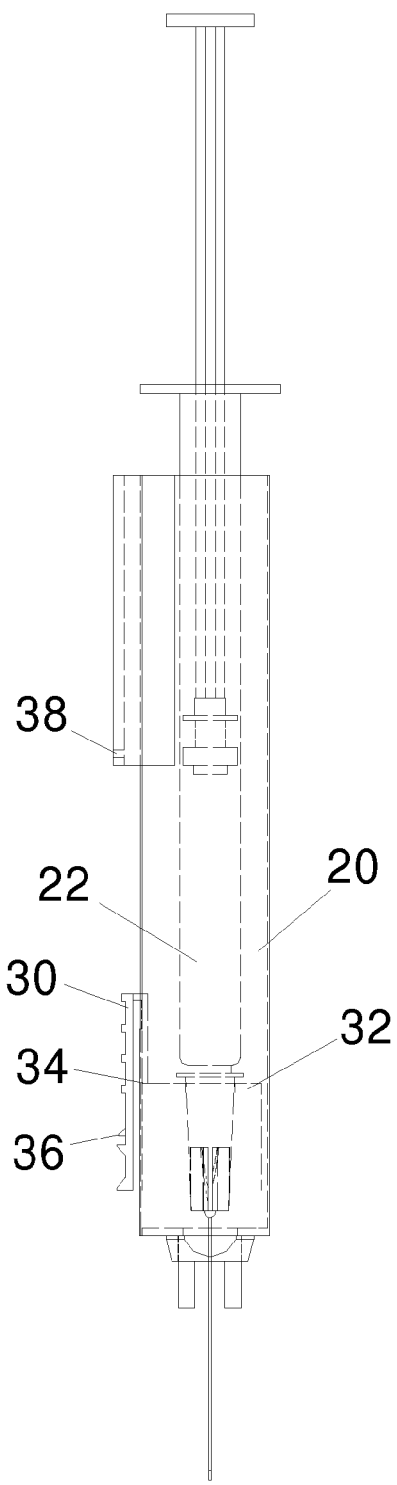
FIG. 1B is a transparent planar view of the device in FIG. 1A.

Looking now at FIG. 1B, syringe holder 32 retains syringe 22 within slot 20. Slot 20 channels syringe holder 32 along a straight pathway so that the needle enters and exits a targeted artery along a consistent axis. The device can be configured to retain any one of a large variety of syringes having various sorts of needles and various sorts of blood receptacles including multi-chamber blood receptacles, capillary pipettes, and flexible tubes. Syringe holder arm 30 attaches to syringe holder 32 at point 34. The syringe holder arm is an extension of the syringe holder. Locking tooth 36 protrudes from syringe holder arm 30. Locking tooth 36 is designed to engage into housing bridge notch 38 to lock arm 30 in place when each is properly aligned.

Figure 2:
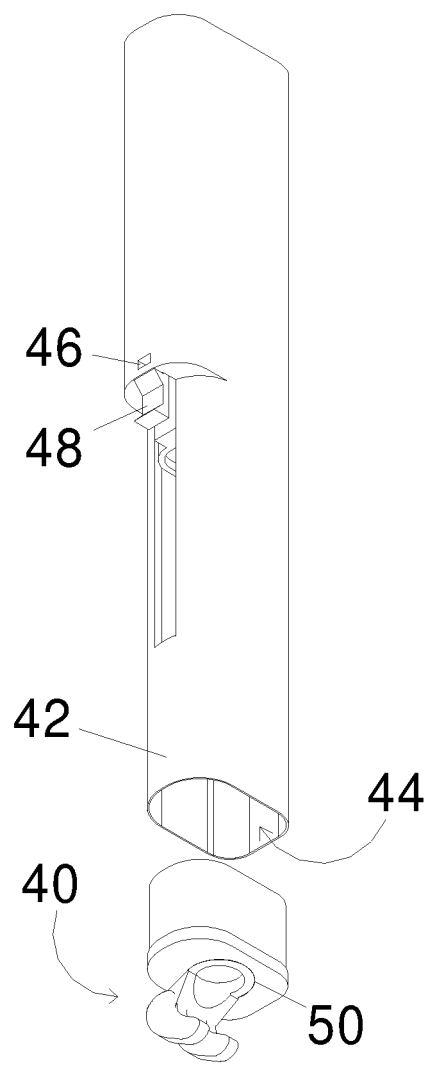
FIG. 2 is a perspective view of an alternative embodiment with a detachable artery stabilizer.

Turning next to FIG. 2, artery stabilizer 40 is detachable from housing 42. Artery stabilizer 40 can be inserted into or removed from within slot 44; this facilitates the manufacturing and assembly of the device, and also provides an option for a technician to reuse the device by installing a clean new artery stabilizer for each patient. The locking tooth (not visible) is locked within housing bridge notch 46 while syringe holder arm 48 is positioned as shown. The technician would press down on syringe holder arm 48 to disengage the locking tooth from within notch 46. Swivel hinge 50 allows the technician to position housing 42 in multiple positions coaxially relative to the stabilizer fingers, allowing for left or right hand use.

Figure 3A:
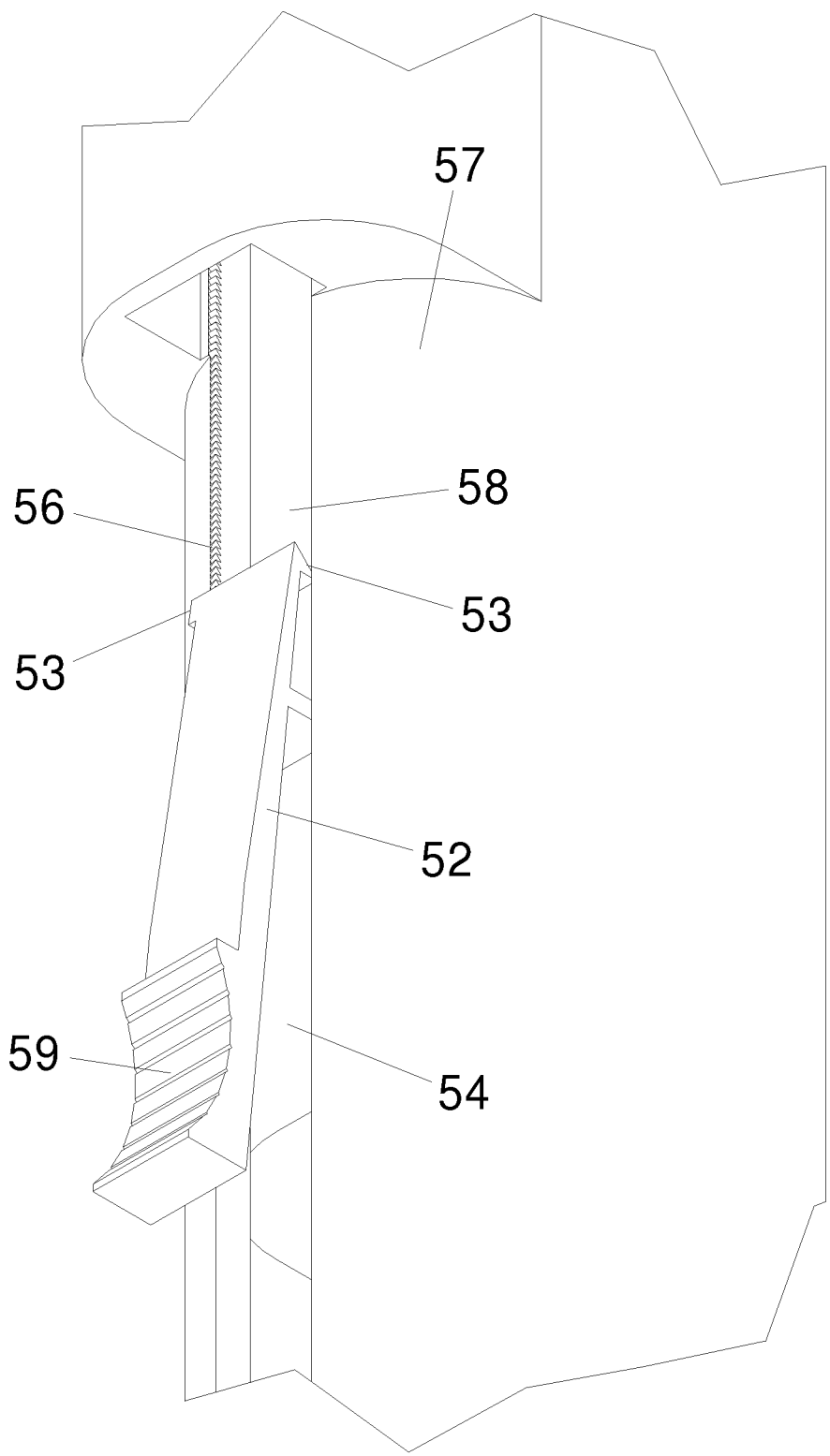
FIG. 3A is an enlarged partial perspective view of an alternative syringe holder arm that utilizes a locking tooth which locks within a series of notches cut into the housing.

Looking at FIG. 3A, syringe holder arm 52 emanates from syringe holder 54 and includes locking tooth 53 which engages within one notch of the series of notches 56 which are cut along a linear path within housing 57 near slit 58; this acts as a syringe lock because syringe holder arm 52 is locked in place within the notch, thereby holding syringe holder 54 in place. The technician presses down finger contact 59 to elevate tooth 53 from within the notch, freeing syringe holder 54 to be moved up or down the housing slot.

Figure 3B:
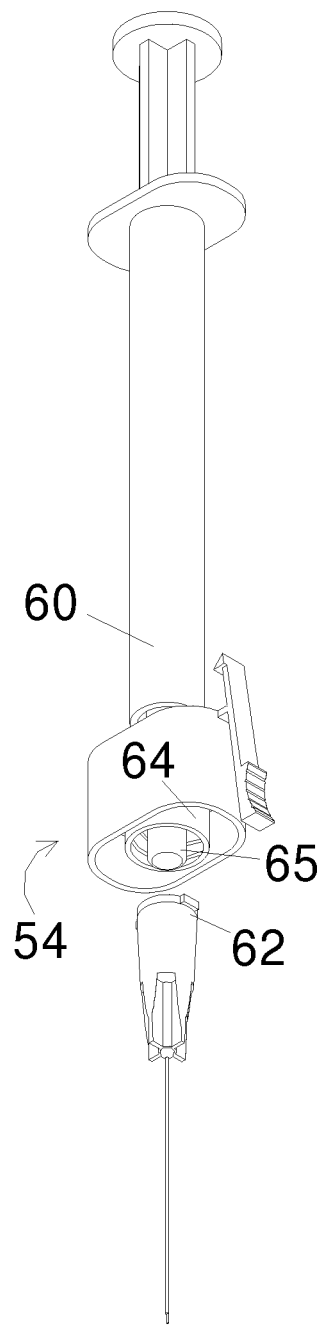
FIG. 3B is a lower perspective view showing how a syringe is attached to the syringe holder.

Turning now to FIG. 3B, syringe holder 54 is designed to retain syringe blood receptacle 60 at one end and needle hub 62 at the opposite end. Syringe holder 54 includes needle hub holder 65 and is provided with a threaded connector designed to retain needle hub 62 via a twist-lock connection; needle hub 62 may be screwed onto or off of needle hub holder 65. An alternative sort of needle hub holder does not have threads, and the needle hub is simply pressed onto the needle hub holder until it is seated there securely. The needle hub of a needle may alternatively be permanently molded to the needle hub holder by the manufacturer. The syringe may be installed at the factory by the manufacturer, or by the technician prior to use.

Figure 3C:
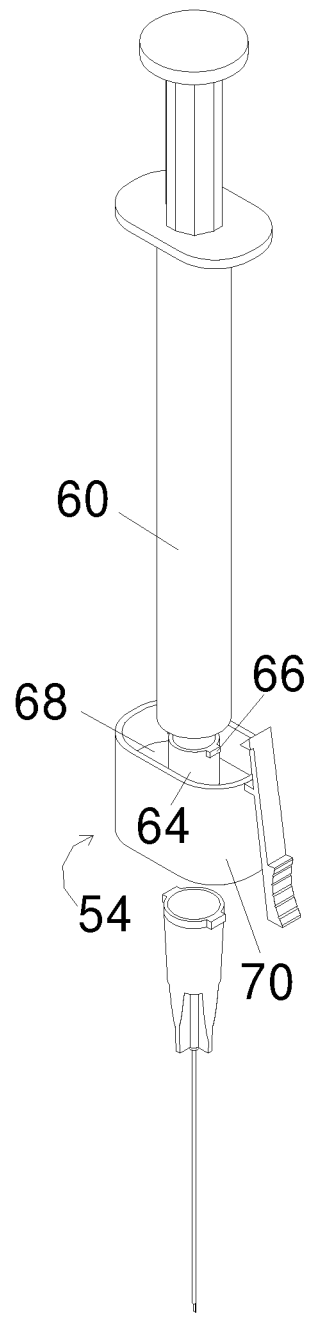
FIG. 3C is an upper perspective view showing how a syringe is attached to the syringe holder.

Turning to FIG. 3C, syringe holder 54 includes blood receptacle holder 64 within which the needle hub adapter component of blood receptacle barrel 60 can be interlocked. This embodiment allows a needle hub adapter with threads to screw over the tabs 66 of blood receptacle holder 64. It also allows a needle hub adapter without threads to be simply pressed into place within the aperture of blood receptacle holder 64. As an alternative, a capillary pipette can be accommodated with an appropriately shaped hub here. Any of a multitude of syringes can be accommodated with an appropriately modified syringe holder. Syringe holder retaining wall 68 holds blood receptacle holder 64 within syringe holder shell 70.

Figure 4:
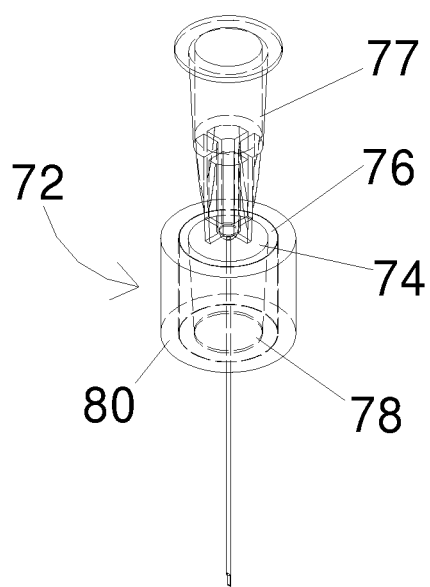
FIG. 4 is a transparent perspective view of an alternative needle hub holder.

Turning next to FIG. 4, alternative needle hub holder 72 retains a syringe in a different manner than the one in FIG. 3B and FIG. 3C. A hypodermic needle is inserted through the opening at the top end 74 of bore 76 until needle hub 77 is securely seated within bore 76. Bore 76 may be composed of a rubbery material which expands just enough to allow a snug fit of needle hub 77 within bore 76, or it may be a solid material which may further be detailed with ridges or knobbies to grip needle hub 77. Bore 76 is tapered so that the bottom end 78 is narrower than top end 74 for a snug fit around needle hub 77. In this embodiment, which utilizes a rubber bore, bore 76 is nested within alternative needle hub holder shell 80. When properly installed, the blood receptacle adapter at the top end of needle hub 77 is left protruding above bore 76 to allow the technician to connect or remove a syringe blood receptacle barrel from needle hub 77. To clarify, the drawing shows only part of the syringe holder; alternative needle hub holder shell 80 would be connected to the rest of the syringe holder in the actual device.

Figure 5A:
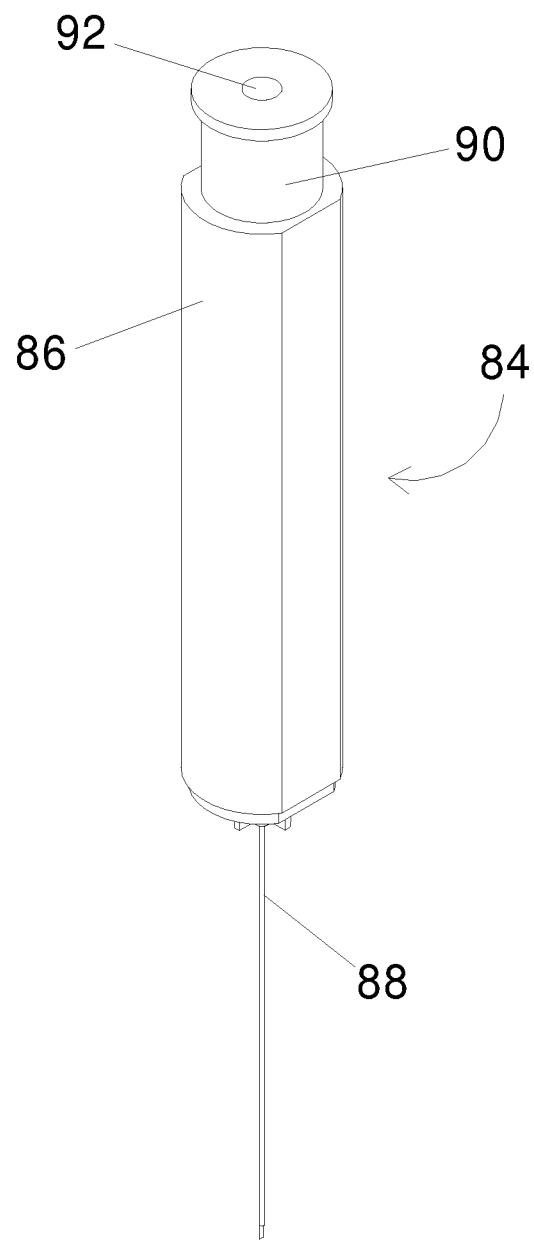
FIG. 5A is a perspective view of an alternative syringe used in an alternative embodiment.

Looking at FIG. 5A now, special syringe 84 includes blood receptacle 86 and needle 88. Access port plug 90 covers an access port (not shown) at the top end of blood receptacle 86. Air vent 92 is situated within plug 90.

Figure 5B:
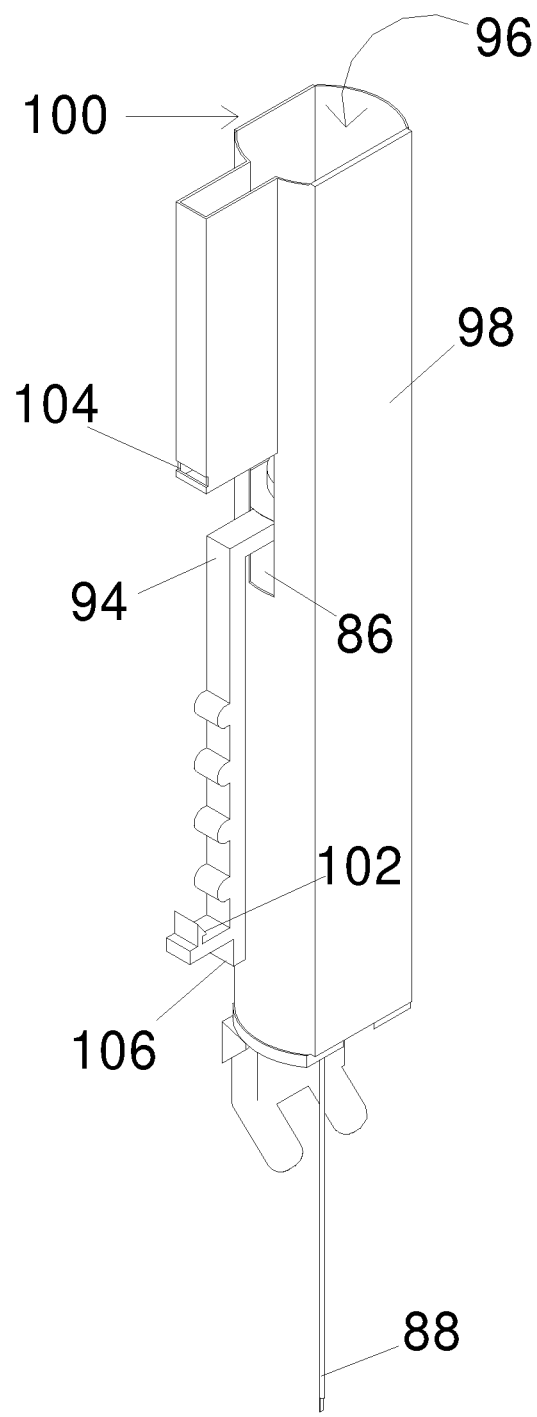
FIG. 5B is a perspective view of the alternative embodiment referred to in the description for FIG. 5A.

Turning to FIG. 5B, syringe holder arm 94 emanates from blood receptacle 86. Blood receptacle 86 is shaped to slide within slot 96 of housing 98. Whereas we describe a syringe holder in the prior descriptions, in this case the blood receptacle is manufactured specifically for placement within housing 98, so the exterior wall of the blood receptacle acts as the syringe holder. Syringe holder arm 94 is contacted by the technician to maneuver the syringe within housing 98. The access port plug would be exposed above top end 100 of housing 98 when locking tooth 102 is engaged within housing bridge notch 104, and needle 88 would be safely positioned within housing 98 to prevent injuries. Locking tooth 102 is engaged by the technician over the top of notch 104, rather than beneath notch 104, in this embodiment. To disengage the lock, the technician would lift up tip 106 in order to extract tooth 102 from notch 104, and then the technician would slide syringe holder arm 94 down to eventually maneuver needle 88 into the targeted artery. A needle tip plug can be added to prevent blood leakage out of the needle tip when the access port plug is removed from the access port.

Figure 6A:
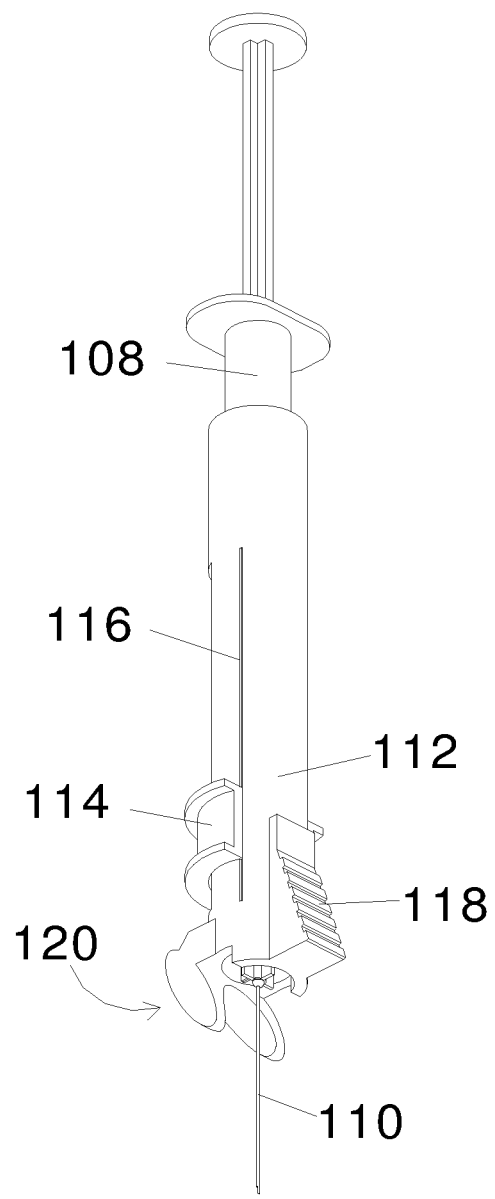
FIG. 6A is an upper perspective view of another alternative embodiment.

Turning now to FIG. 6A, syringe 108 is attached to syringe holder 114 within housing 112. Syringe holder 114 slides up and down housing 112 along support track 116. When syringe holder 114 is maneuvered all the way it can travel up housing 112, syringe holder 114 locks in place there, holding the sharp tip of needle shaft 110 safely within the protective walls of housing 112. The technician presses down on finger hold platform 118 to press artery stabilizer 120 down over a targeted artery.

Figure 6B:
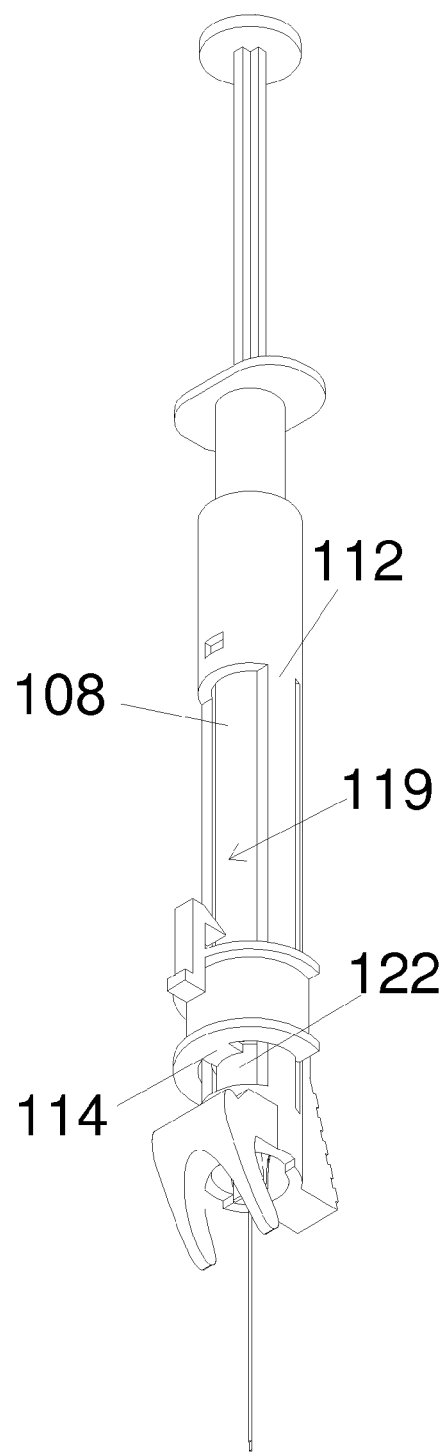
FIG. 6B is a lower perspective view of the embodiment in FIG. 6A

Referring now to FIG. 6B, syringe holder 114 passes through housing slit 119. Slit 119 is cut within housing 112. Alternatively, syringe holder 114 can travel within a track cut within the interior of housing 112, or the inside of housing 112 can have a unique shape through which a similarly shaped syringe holder can be conveyed. Either way, housing 112 channels the syringe holder along a straight pathway so that the needle enters and exits a targeted artery along a consistent axis. A syringe may be supplied and installed with the device by the manufacturer, or the technician may be responsible for installing a syringe prior to use.

Figure 7:
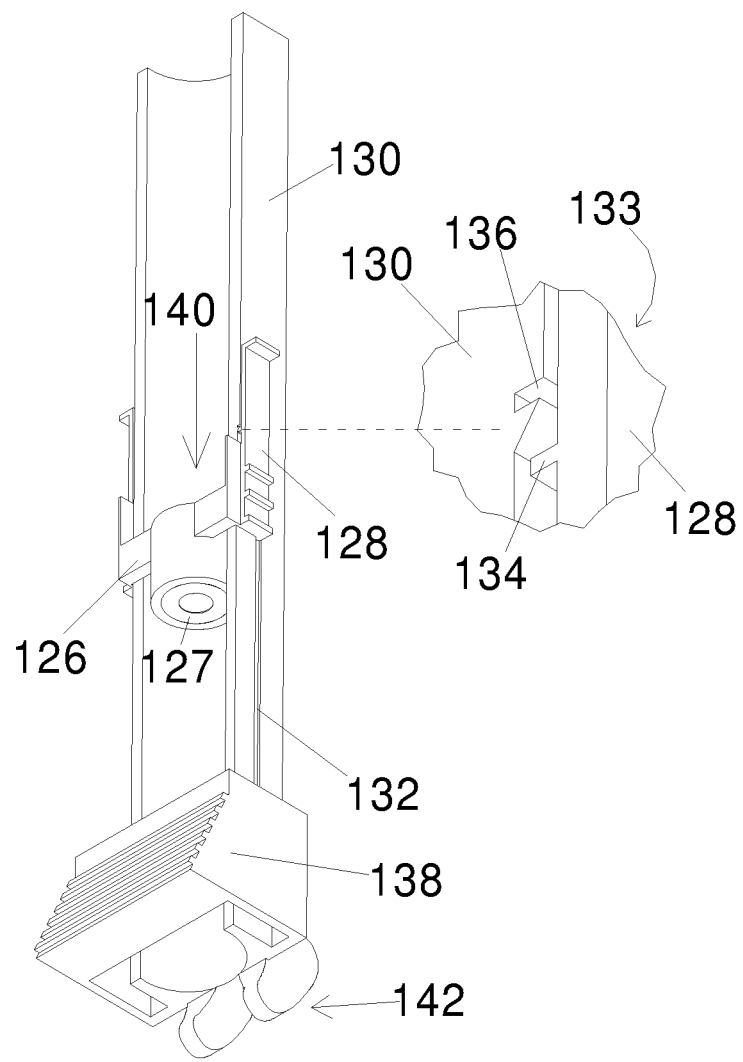
FIG. 7 is a perspective view of another alternative embodiment, including an exploded partial view of the syringe lock.

Looking at FIG. 7, syringe holder 126 is slidably connected to shaft 130. Support track 132 allows syringe holder 126 to be moved up and down shaft 130. Alternatively the syringe holder can snap directly onto each side of the shaft, and so the sides of the shaft act as the support track. Syringe lock 133 allows for automatic engagement of tooth 134, which is integrated on syringe holder arm 128, within notch 136; this holds the needle of a syringe locked in place behind needle shield 138. Notch 136 is cut within shaft 130. Prior to use, the technician inserts a syringe down through the upper opening 140 of needle hub holder 127 so that the needle passes through the opening and the hub of the needle becomes securely seated within needle hub holder 127. Alternatively, the device can be supplied with a syringe that is preinstalled on the device by the manufacturer. The technician can press down on shield 138 to lodge artery stabilizer 142 over a targeted artery.

Figure 8:
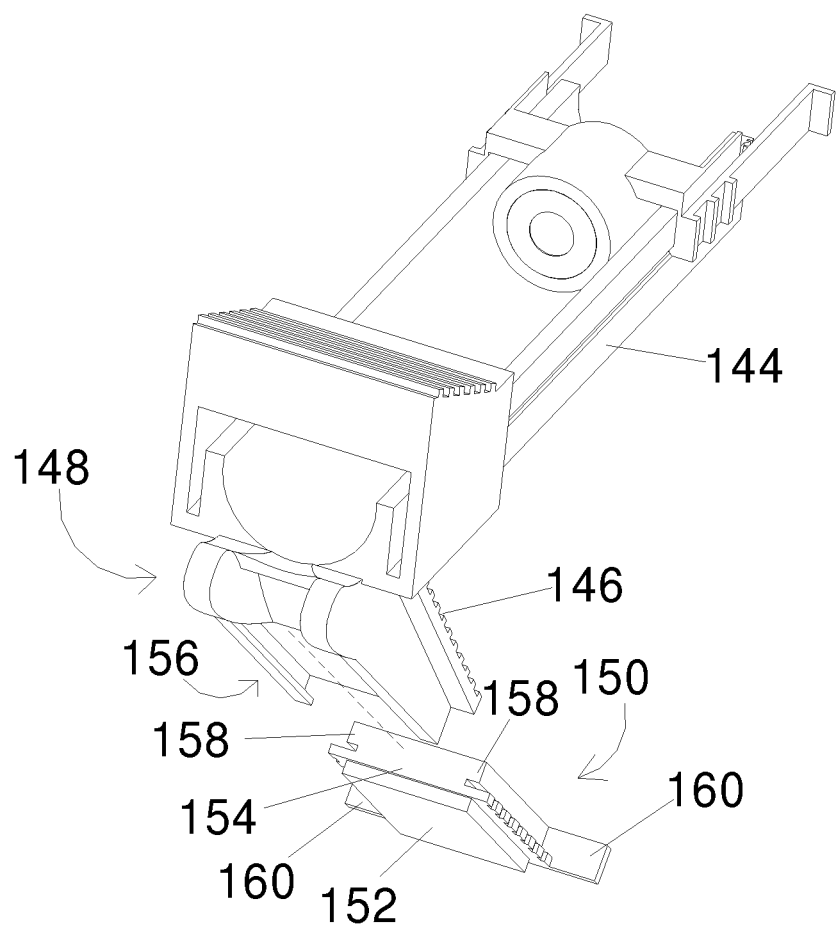
FIG. 8 is a slightly enlarged lower perspective view of another alternative embodiment which includes a removable gauze holder.

Referring next to FIG. 8, shaft 144 is shorter than the shaft in FIG. 7 to illustrate that its length can be any one of various lengths. Finger-hold platform 146 protrudes from its connection to shaft 144. The technician presses down platform 146 to apply artery stabilizer 148 over a targeted artery. Gauze dressing member 150 includes gauze pad 152 which is attached to the bottom of gauze holder 154. Gauze dressing member 150 can be installed or removed from within gauze holder track 156 which is integrated beneath platform 146. Gauze holder edges 158 are shaped to slide into gauze holder track 156. After the needle insertion procedure, the technician can move the device over the wound and apply gauze pad 152 on the wound to dress it. By retaining graspable tabs 160, the technician can slide the rest of the device off of dressing member 150, leaving just dressing member 150 over the wound. Dressing member 150 can then be taped down over the wound.

Figure 9A:
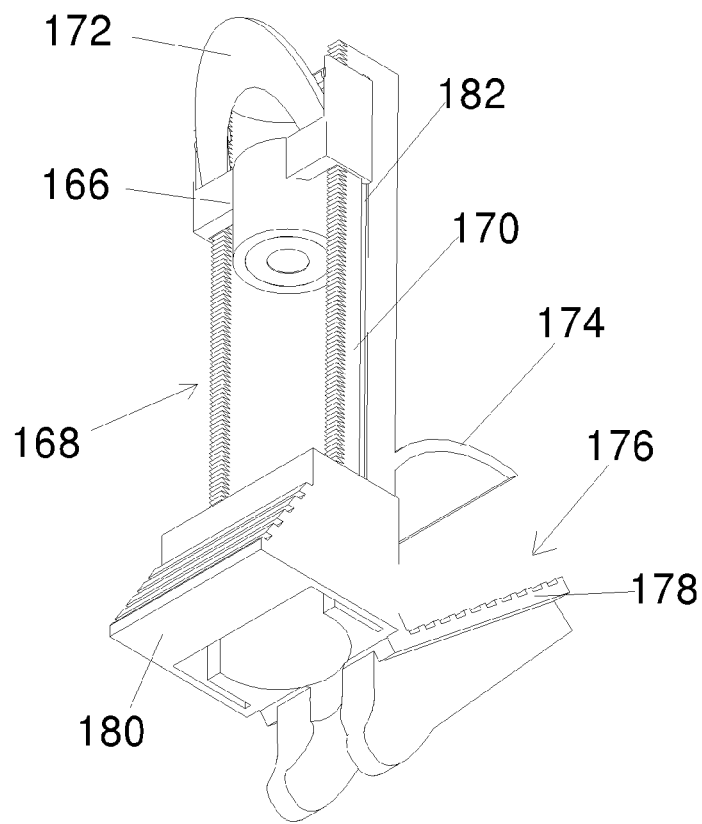
FIG. 9A is a perspective view of an alternative syringe guide utilizing a series of notches to lock in place the syringe holder arm and attached syringe holder.

Looking at FIG. 9A now, syringe holder 166 can be locked in place in multiple locations as a result of the series of notches 168 cut within shaft 170. Syringe holder arm 172 is pressed down by the technician to release an integrated tooth from its position within one of the notches. One of the technician's fingers, preferably a thumb, is held in place between flexible clip 174 and the top surface 176 of platform 178, helping the technician wield the device during the procedure. As with prior embodiments, a syringe is installed within syringe holder 166 by the technician or the manufacturer. The tip of the needle of the syringe would be situated safely under the protective walls of needle shield 180 before and after the needle insertion procedure for safety. Support track 182 holds syringe holder 166 stably on shaft 170.

Figure 9B:
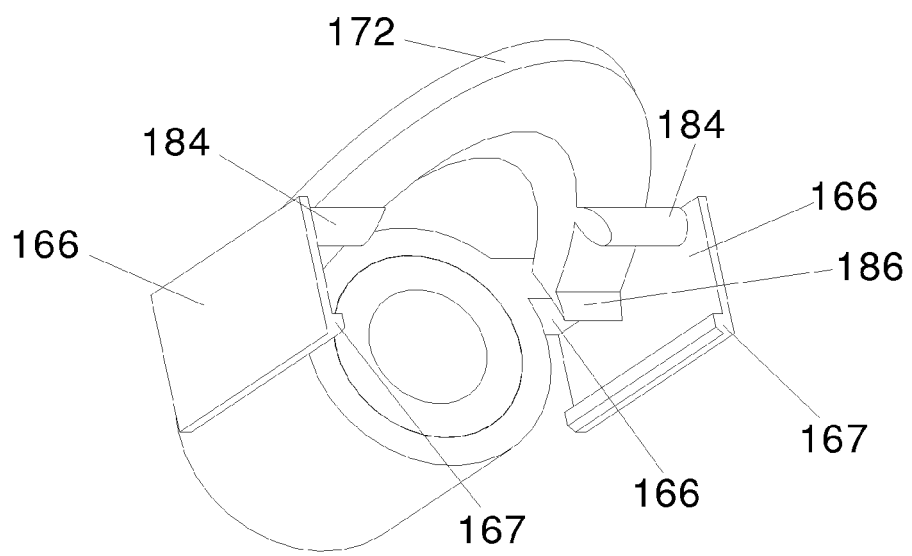
FIG. 9B is an enlarged rear perspective view of the syringe holder arm connected to the syringe holder of the device shown in FIG. 9A.

Turning next to FIG. 9B, syringe holder 166 includes protrusions 167 which would fit within the support track (not shown). Syringe holder arm 172 is attached to each side of syringe holder 166 by hinge 184. Tooth 186 moves upward as syringe holder arm 172 is pressed down by the technician, freeing syringe holder 166 for movement up or down the shaft (not shown).

Figure 10:
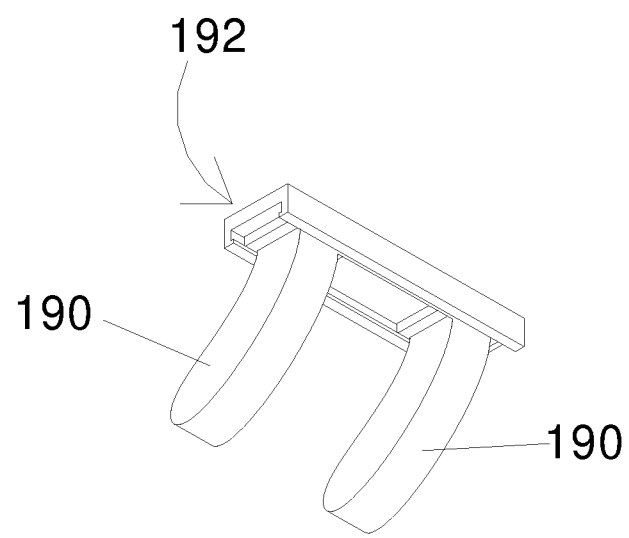
FIG. 10 is an enlarged lower rear perspective view of an alternative artery stabilizer with each stabilizer finger situated within an adjustment track to allow adjustability of the distance between each finger.

Turning finally to FIG. 10, stabilizer fingers 190 are slidably situated within artery stabilizer adjustment track 192 so that the distance between each finger can be altered to accommodate various sizes of targeted arteries. It can be designed as a more complex apparatus, such as one which requires the technician to turn a knob to alter the distance between each finger, but a simple one is shown here for ease of illustration.

What is claimed is:

1. A syringe guide comprising an elongated rigid body that comprises a distal end, a proximal end, and a linear channel disposed along at least part of its length;
    a syringe holder comprising a needle hub holder that comprises a mating surface with a proximal end and a distal end, said mating surface defining a taper from said proximal end to said distal end, whereby said mating surface grips a corresponding mating surface of a needle hub component of a hypodermic needle when said mating surface of said needle hub holder and said mating surface of said needle hub are arranged for surface to surface contact, and a channel link component shaped to slide stably along said linear channel when said needle hub holder is maneuvered up or down said elongated rigid body; and
    a blood vessel stabilizer comprising at least one stabilizer finger connected to said distal end of said elongated rigid body whereby said channel positions a needle attached to said needle hub holder in line over a length of a target blood vessel while said stabilizer finger is pressed down lengthwise adjacent to one side of said length of said blood vessel.

2. The device of claim 1 wherein said blood vessel stabilizer comprises two stabilizer fingers and said stabilizer fingers are positioned on said elongated rigid body so that said needle hub holder positions an attached needle to pass between said stabilizer fingers as said needle hub holder is moved toward said distal end of said elongated rigid body.

3. The device of claim 1 wherein said needle hub holder comprises a structure with a hollow bore, said hollow bore comprising a proximal end and a distal end, said distal end of said hollow bore having a smaller diameter than said proximal end.

4. A syringe guide comprising an elongated rigid body that comprises a distal end, a proximal end, and a linear channel disposed along at least part of its length;
    a needle hub holder comprising an aperture adapted to grip a portion of a needle hub of a hypodermic needle, said needle hub holder comprising a rigid wall structure and a resilient material retained by said rigid wall structure wherein said resilient material comprises a mating surface that defines the boundaries of said aperture, and said mating surface when engaged with said portion of said needle hub conforms to a contacted surface of said portion of said needle hub while said rigid wall structure remains rigid and retains its original form, said needle hub holder further comprising a channel link component shaped to slide stably and axially along said linear channel; and a blood vessel stabilizer comprising at least one stabilizer finger connected to said distal end of said elongated rigid body whereby said channel positions a needle attached to said needle hub holder in line over a length of a target blood vessel while said stabilizer finger is pressed down lengthwise adjacent to one side of said length of said blood vessel.

5. The device of claim 4 wherein said blood vessel stabilizer comprises two stabilizer fingers and said stabilizer fingers are positioned on said elongated rigid body so said needle hub holder positions an attached needle to pass between said stabilizer fingers as said needle hub holder is moved toward said distal end of said elongated rigid body.

6. The device of claim 4 wherein said aperture comprises a bore with a proximal end and a distal end, said distal end of said bore having a smaller diameter than said proximal end.

7. A syringe guide comprising an elongated rigid body that comprises a distal end, a proximal end, and a linear channel disposed along at least part of its length;
    a hypodermic needle comprising an elongated rigid tube attached to a needle hub, said needle hub comprising a mating surface with a selected shape;
    a needle hub holder comprising a mating surface that corresponds to said shape of said mating surface of said needle hub whereby when mated said mating surface of said needle hub holder firmly grips said mating surface of said needle hub, said needle hub holder further comprising a channel link component shaped to slide stably and axially along said linear channel; and
    a blood vessel stabilizer comprising at least one stabilizer finger connected to said distal end of said elongated rigid body whereby said channel positions said needle in line over a length of a target blood vessel while said stabilizer finger is pressed down lengthwise adjacent to one side of said length of said blood vessel.

8. The device of claim 7 wherein said blood vessel stabilizer comprises two stabilizer fingers and said stabilizer fingers are positioned on said elongated rigid body so that said needle hub holder positions an attached needle to pass between said stabilizer fingers as said needle hub holder is moved toward said distal end of said elongated rigid body.

\* \* \* \* \*